United States Patent [19]

Heidemann

[11] 4,019,761
[45] Apr. 26, 1977

[54] CONNECTION FOR FOAM INSULATED PIPES

[75] Inventor: Gerrit Heidemann, Oldenzaal, Netherlands

[73] Assignee: Industriele Onderneming Wavin N.V., Zwolle, Netherlands

[22] Filed: Jan. 7, 1972

[21] Appl. No.: 216,052

[30] Foreign Application Priority Data

Jan. 8, 1971    Netherlands ................... 7100216

[52] U.S. Cl. .................................. 285/47; 285/286; 285/381
[51] Int. Cl.² ........................................ F16L 59/14
[58] Field of Search ......... 285/47, 53, 381, DIG. 5, 285/286, 236, 230, 288, 47

[56] References Cited

UNITED STATES PATENTS

| | | | |
|---|---|---|---|
| 2,416,618 | 2/1947 | Ferla | 285/288 X |
| 2,761,949 | 9/1956 | Colton | 285/47 X |
| 2,894,538 | 7/1959 | Wilson | 285/53 |
| 2,964,064 | 12/1960 | Jones | 285/47 |
| 3,146,005 | 8/1964 | Peyton | 285/47 |
| 3,369,826 | 2/1968 | Boosey et al. | 285/47 |
| 3,453,716 | 7/1969 | Cook | 285/286 X |
| 3,502,356 | 3/1970 | Schmunk | 285/230 |
| 3,544,672 | 12/1970 | Goda et al. | 285/381 X |
| 3,711,124 | 1/1973 | Gerholt et al. | 285/47 |

FOREIGN PATENTS OR APPLICATIONS

| | | | |
|---|---|---|---|
| 92,771 | 11/1968 | France | 285/47 |
| 2,028,054 | 1/1971 | Germany | 285/47 |
| 1,080,305 | 8/1967 | United Kingdom | 285/235 |

Primary Examiner—Thomas F. Callaghan
Attorney, Agent, or Firm—Haseltine, Lake & Waters

[57] ABSTRACT

A pipe having an annular ring of a foam plastic material on its outer surface and a covering layer of thermoplastic material on the outer surface of the foam plastic ring. An opening between two free ends of foam plastic layer ring lying opposite each other of adjoining pipes is closed by a connecting layer which cooperates sealingly with the covering layers. A ring of rigid material is positioned under the covering layer at the point where the connecting layer is clamped onto the covering layer.

3 Claims, 1 Drawing Figure

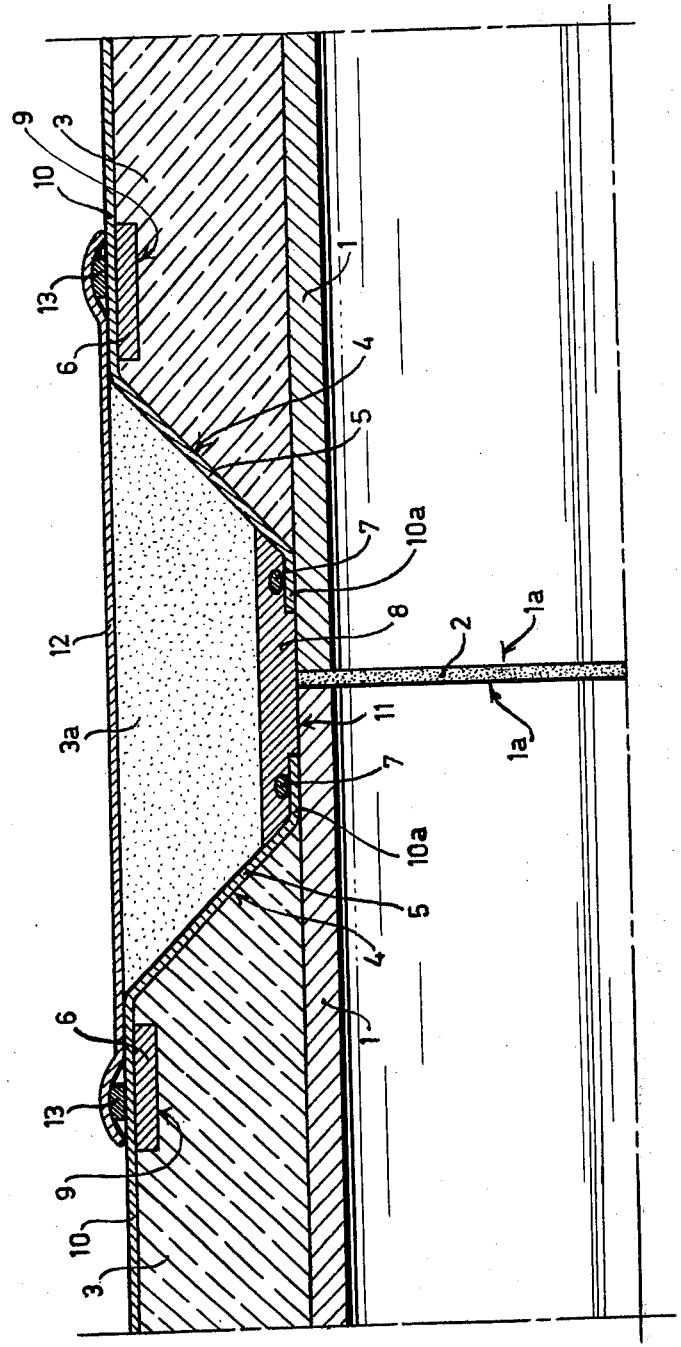

CONNECTION FOR FOAM INSULATED PIPES

The invention relates to a connection for pipes provided with an external foam plastic layer at its ends, the latter being provided with a finishing layer. The space between separate ends of the foam plastic layer being enclosed by a cover layer which is clamped onto the separate ends of the foam plastic layers and which on either side, at a distance from the space, cooperates with the finishing layer, at least one elastical seal being provided between the finishing layer and the cover layer.

Such a connection of two metal pipes provided with a foam plastic layer, preferably a polyurethane foam plastic layer, with a finishing layer of thermoplastic material is known.

In these known connections, the finishing layer may consist of a polyethylene layer which is obtained by winding a hot polyethylene tape, issuing from an extruder, in an overlapping fashion around the insulating foam plastic layer. Due to the high temperature of the polyethylene, the overlapping parts of the tape-shaped polyethylene material are sealed together.

In order to permit the metal pipes to be welded together, the foam plastic layer terminates at a distance from the pipe ends. The space formed between two adjacent pipes after they have been welded together is subsequently filled with foam plastic, whereupon a sleeve extending beyond the space formed between the two interconnected pipes is shrunk onto the finishing layer. For that purpose a sleeve of thermoplastic material such as polyvinylchloride is used. In order to ensure a proper sealing it is usual to provide an elastic sealing material, e.g. a rubber ring, between the outer surface of the finishing layer and the sleeve of thermoplastic material shrunk thereon.

It has been found that this sealing, especially when the finishing layer is a soft polyethylene tape, is not entirely leak-proof when a shrunk-on sleeve of polyvinylchloride is applied. This is presumably caused by the fact that owing to the pressure exerted by the shrunk-on sleeve of polyvinylchloride on the polyethylene layer, the latter tends to flow out. Due to this flowing out phenomena also called "creep," to the seal between the rubber ring and the outer surface of the finishing layer, and the inner surface of the cover layer is lost.

It is an object of the invention to obviate these difficulties by providing a circular layer of rigid material under the finishing layer, at least in one area in which the finishing layer and the cover layer face each other and preferably in the area where the elastic seal ring is situated.

By rigid material is understood a material with an E modulus greater than that of polyethylene or polyvinylchloride, while the material does not shrink at the pressure exerted by the shrunk-on sleeve of polyvinylchloride.

The cylindrical layer of rigid material is advantageously embedded in the foam plastic layer and the cylindrical layer consists of steel, hard polyvinylchloride, glass fibre reinforced thermosetting synthetic resin or similar material.

The material for the cylindrical layer of rigid material should, however, be selected in such a way that it absorbs the forces exerted by the shrunk-on sleeve of thermoplastic material such as polyvinylchloride in such a way that there is no leakage.

The invention will be described in greater detail with reference to the drawing in which the sole FIGURE is a cross-section of an embodiment of the connection according to the invention.

According to the FIGURE, the ends 1a of two metal pipes 1 are interconnected by a welded joint 2. It is obvious that instead of metal pipes 1 plastic pipes can be used, which in a suitable way, can be sealed together.

Provided around each pipe is an insulating layer 3 of polyurethane foam plastic on which a finishing layer 10 is disposed. This finishing layer is obtained, for example, by winding warm polyethylene tape or similar thermoplastic materials, issuing from an extruder, around the foam plastic layer, the parts of such a tape, which overlap each other, being interconnected under the influence of the temperature and the plastic conditions of the polyethylene to form a gas-tight and waterproof finishing layer.

A foam plastic insulation 3a is provided on the two interconnected metal pipes 1 between the ends of the foam plastic layer. The insulation 32 may also consist of polyurethane foam plastic, but other foam plastics may be employed which are different from the foam plastic layer 3. If desired, the insulating layer 3a may also consist of a material other than a foam plastic layer.

The space between the ends of the foam plastic layer can also be filled with fibres of mineral wool, or, the insulating layer 3a may consist partially of a foam plastic and partially of a non-expanded plastic, e.g. a thermosetting resin such as an epoxy resin. Also polyurethane plastic in a non-expanded shape may be considered. Before interconnecting the pipes 1 by means of the welded joint, a ring of elastic material 13 is provided on the outer surface of the finishing layer 10. This ring can be composed of rubber, compressed tape, or similar material. A widened pipe section 12 is slid over the ring. The section 12 can be made of polyvinylchloride, polyethylene or other thermoplastic material, the inner diameter of this pipe section being initially greater than the outer diameter of the ring 13 after placement on the finishing layer 10. When heated, the widened section 12 will, however, shrink and start co-operating with the sealing ring 13, whereby a gastight and waterproof connection is obtained. Instead of the pipe section 12 also, a tubular foil part can be used.

Due to the forces exerted by the shrunk-on pipe section 12, a deformation of the finishing layer 10 is sometimes produced after a period of time at the location of the ring or at other locations where the shrunk-on pipe section 12 cooperates with the outer surface of the finishing layer 10.

In order to overcome this deficiency a metal ring 6 is provided in the foam plastic layer 3 which ensures that deformation of the shrunk-on section 12 and the foam plastic situated thereunder due to the pressure of the shrunk-on section 12 on the sealing ring 13 cannot be produced.

The ring 6 may consist of metal, hard polyvinylchloride, or a fibre-reinforced thermosetting resin.

The ring 6 is embedded in a recess 9 of the foam plastic.

In order to improve the connection, is is advisable to bevel the foam plastic layer 3 at its ends to form inclined walls 4, whereupon the finishing layer 10 is further wound to form portion 5 in such a way that an end part 10a thereof extends on the wall 11 of the steel pipe 1.

In order to prevent leakages which could give rise to moisture penetrating into the insulating part 3a along the end part 10a of the finishing layer, it is advisable to provide an elastic rubber seal 7 on the end part 10a of the finishing layer, whereupon by subsequently winding glass fibres impregnated with a thermosetting resin around the end part 10a of the finishing layer, a thermosetting glass fibre-reinforced resin layer 8 is obtained. This thermosetting resin layer 8 should at least extend from the area of the part of the metal pipe which is not covered by the end part 10a of the finishing layer to the area over the said end part 10a. Such a glass fibre-reinforced thermosetting resin layer is advantageous in that the seal is improved, since glass fibre reinforced thermosetting resins, particularly epoxy resins, adhere excellently to steel or a metal surface treated with an epoxy resin, so that between the outer surface of the metal pipe and the part cooperating therewith of the finishing layer 10 of polyethylene, particularly the part 10a, an absolutely moisture proof sealing is ensured.

It should be noted that the finishing layer 10 may also be obtained by wrapping a non-heated tape of polyethylene around the foam layer and connecting the overlapping parts by heat sealing.

At last, it should be emphasized that pipe section 12 might be integral with and of the same plastic material as the finishing layer 10, on the right tube as shown in the right part of the FIGURE. In that case the right part 5 as shown in the FIGURE is not present so that foam plastic part 3 is integral with the foam plastic 3 in the right part when the ends of the plastic foam layer consist of hollow tubes which are slid over the metal pipes 1. The overlapping part of section 12 in the region of sealing ring 13 in the left part of the FIGURE is then the only part to be connected tightly with the finishing layer 10 on the left pipe 3. This connection may also be obtained with separate clamping means such as a steel band (not shown) which cooperates with the overlapping part of section 12 opposite the sealing ring 13 in the left part of the FIGURE. In the case of using separate hollow tubes of foam plastic, it is advisable to provide the left tube of foam plastic 3 with a finishing layer comprising left layer 10 and layer 8 which is clamped onto the pipe 1 and to slide a second tube comprising the right foam layer 3 together with 3a as one part over the pipe against the left foam plastic tube 3. The right and left foam plastic tubes 3 are preferably provided with mated ends.

What I claim is:

1. A pipe connection comprising two aligned pipes having opposed ends which are secured together, each pipe including an external layer of foam plastic material thereon, said layer of foam material not extending to the end of the respective pipe so that the layers on the secured pipes define a space therebetween, a finishing cover layer of thermoplastic material on each said foam layer, said finishing layer being of substantially uniform thickness, an elastic sealing ring mounted on the finishing layer on each pipe proximate the end thereof, a sleeve enclosing said space and having ends surrounding the rings, said sleeve being heat shrunk onto the finishing layers to compress the sealing rings, said finishing layer of thermoplastic material tending to creep under the pressure applied to the sealing rings, and a ring of rigid material embedded in each layer of foam plastic material underneath the finishing layer in the region of the associated sealing ring to prevent deformation of the finishing layer and presserve the seal thereat, said ring being cylindrical and having a rectangular cross-section of greater thickness than the finishing layer with opposed parallel side surfaces in abutment with the foam plastic material in which it is embedded, a bottom surface resting on the foam plastic material, and an upper surface flush with the upper surface of the foam layer and in contact with said finishing layer.

2. A pipe connection as claimed in claim 1 wherein said ring of rigid material is constituted of steel, hard polyvinylchloride, or a fibre-reinforced thermosetting resin.

3. A pipe connection as claimed in claim 1 comprising a foam plastic material filling said space.

* * * * *